(12) United States Patent
Yamamoto et al.

(10) Patent No.: US 11,535,939 B2
(45) Date of Patent: Dec. 27, 2022

(54) SURFACE TREATMENT METHOD FOR COPPER OR COPPER ALLOY, SURFACE TREATMENT LIQUID FOR STERILIZING COPPER OR COPPER ALLOY, AND STERILIZATION METHOD USING COPPER OR COPPER ALLOY TREATED BY SAID METHOD

(71) Applicant: NATIONAL INSTITUTE FOR MATERIALS SCIENCE, Ibaraki (JP)

(72) Inventors: Akiko Yamamoto, Ibaraki (JP); Keiichiro Oishi, Tokyo (JP); Shinji Tanaka, Tokyo (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 372 days.

(21) Appl. No.: 16/627,867

(22) PCT Filed: May 30, 2018

(86) PCT No.: PCT/JP2018/020675
§ 371 (c)(1),
(2) Date: Dec. 31, 2019

(87) PCT Pub. No.: WO2019/008950
PCT Pub. Date: Jan. 10, 2019

(65) Prior Publication Data
US 2020/0157688 A1 May 21, 2020

(30) Foreign Application Priority Data
Jul. 3, 2017 (JP) .............................. JP2017-130373

(51) Int. Cl.
*C23C 22/05* (2006.01)
*A01N 37/20* (2006.01)
(Continued)

(52) U.S. Cl.
CPC .............. *C23C 22/05* (2013.01); *A01N 37/20* (2013.01); *A61L 2/235* (2013.01); *A61L 2/238* (2013.01); *C22C 9/04* (2013.01); *C22C 9/10* (2013.01)

(58) Field of Classification Search
CPC ......... C23C 22/05; A01N 37/20; A61L 2/235; A61L 2/238; C22C 9/04; C22C 9/10
See application file for complete search history.

(56) References Cited

U.S. PATENT DOCUMENTS 9,155,310 B2 * 10/2015 Agrawal .............. A61Q 17/005

FOREIGN PATENT DOCUMENTS

JP 53-73516 6/1978
JP 3107399 9/2000
(Continued)

OTHER PUBLICATIONS

Leanne Koster, Indoor humidity and your family's health, Feb. 16, 2016, National Asthma Council (Year: 2016).*
(Continued)

*Primary Examiner* — Anthony J Zimmer
*Assistant Examiner* — Jacob J Gusewelle
(74) *Attorney, Agent, or Firm* — Wenderoth, Lind & Ponack, L.L.P.

(57) ABSTRACT

The present invention provides a surface treatment method that improves antimicrobial activity of copper or a copper alloy and enhances immediate effects of antimicrobial actions on the surface of the copper or the copper alloy. A surface treatment method for copper or a copper alloy according to the present invention comprises preparing a reducing agent solution containing a biological reducing substance, and treating the surface of the copper or the copper alloy with the reducing agent solution. The present invention also provides a surface treatment liquid for ster-
(Continued)

ilizing copper or a copper alloy, in which the surface treatment liquid contains a biological reducing substance. The present invention also provides a sterilization method that comprises bringing copper or a copper alloy treated by the surface treatment method into contact with a surface of an object to sterilize the surface of the object.

10 Claims, 9 Drawing Sheets

(51) Int. Cl.
*A61L 2/235* (2006.01)
*A61L 2/238* (2006.01)
*C22C 9/04* (2006.01)
*C22C 9/10* (2006.01)

(56) References Cited

FOREIGN PATENT DOCUMENTS

JP 2013-209338 10/2013
WO 98/12924 4/1998

OTHER PUBLICATIONS

Gadi Borkow, Jeffrey Gabbay, Putting copper into action: copper-impregnated products with potent biocidal activities, https://faseb.onlinelibrary.wiley.com/doi/epdf/10.1096/fj.04-2029fje, Sep. 2, 2004 (Year: 2004).*

Notice of Reasons for Refusal dated Jul. 21, 2020 in corresponding Japanese Patent Application No. 2019-528406 with English-language translation.

"Product Information—Sodium Ascorbate Solution 112,49 mg/mL", Grupo Gales Medicina Preventiva LTDA, Jan. 2011, XP055326279, Retrieved from the Internet: URL: http://www.hugogalindosalom.com/images/pdf/inserto.pdf [retrieved on Dec. 6, 2016].

"Safety Data Sheet: Sodium Sulfite Solution", Ineos Calabrian, Sep. 2016, pp. 1-7, XP055778789, U.S.A., Retrieved from the Internet: URL: https://www.ineos.com/globalassets/ineos-group/businesses/ineos-enterprises/businesses/ineos-calabrian/resource-center/safety-data-sheets/sodium_sulfite_solution_sds_2016.pdf [retrieved on Feb. 23, 2021].

"Product Information: L-Glutathione reduced, Product No. G4251", Sigma-Aldrich, May 2006, pp. 1-2, XP055778793, U.S.A., Retrieved from the Internet: URL: https://www.sigmaaldrich.com/content/dam/sigma-aldrich/docs/Sigma-Aldrich/Product_Information_Sheet/g4251pis.pdf [retrieved Feb. 23, 2021].

"Omegapharm Acetylcysteine Solution for Inhalation", MIMS, Dec. 2014, pp. 1-2, XP055778795, Australia, Retrieved from the Internet: URL: https://www.nps.org.au/assets/medicines/b4465490-33a2-4f35-ae73-a53300ff9fc2-reduced.pdf [retrieved Feb. 23, 2021].

"Supporting document 1: Risk and technical assessment report—Application A1117", Food Standards, Jun. 2016, pp. 1-9, XP055778806, Australia, Retrieved from the Internet: URL: https://www.foodstandards.gov.au/code/applications/Documents/A1117%20L-cysteine%20as%20a%20FA%20CFS%20SD1.pdf [retrieved on Feb. 23, 2021].

G. Grass et al., "Metallic Copper as an Antimicrobial Surface", Applied and Environmental Microbiology, Dec. 2010, vol. 77, No. 5, pp. 1541-1547.

Extended European Search Report dated Mar. 4, 2021 in corresponding European Patent Application No. 18828403.8.

International SearchReport (ISR) dated Jul. 10, 2018 in International Application No. PCT/JP2018/020675.

Shigetoshi Kobuchi et al., "Analysis of Antimicrobial Activity of the Surface of 1B Family Transition Metal Plates", Corrosion Engineering, vol. 52, pp. 428-435, 2003, together with machine translation.

Nadine J. Ragab-Depre, "Water Disinfection with the Hydrogen Peroxide-Ascorbic Acid-Copper(II) System", Applied and Environmental Microbiology, vol. 44, No. 3, pp. 555-560, Sep. 1982.

Michael G. Schmidt, et al., Sustained Reduction of Microbial Burden on Common Hospital Surfaces through Introduction of Copper, Journal of Clinical Microbiology, vol. 50, No. 7, pp. 2217-2223, Jul. 2012, cited in the specification.

Cassandra D. Salgado, et al., "Copper Surfaces Reduce the Rate of Healthcare-Acquired Infections in the Intensive Care Unit", Infection Control and Hospital Epidemiology, vol. 34, No. 5, pp. 479-486, May 2013, cited in the specification.

Akiko Yamamoto, "To reduce the incidence of infection", Sep. 12, 2017, together with machine translation.

* cited by examiner (a)

(b)

SURFACE TREATMENT METHOD FOR COPPER OR COPPER ALLOY, SURFACE TREATMENT LIQUID FOR STERILIZING COPPER OR COPPER ALLOY, AND STERILIZATION METHOD USING COPPER OR COPPER ALLOY TREATED BY SAID METHOD

TECHNICAL FIELD

The present invention relates to a surface treatment method for copper or a copper alloy, a surface treatment liquid for sterilizing copper or a copper alloy, and a sterilization method using copper or a copper alloy treated by the method.

BACKGROUND ART

In recent years, the spread of antimicrobial-resistant bacteria and viruses having resistance to antimicrobials and antivirals has been regarded as a serious problem. A collaborative study between the UK Government and the Wellcome Trust estimates that 10 million people across the world will die by 2050 because of antimicrobial-resistant bacteria (Review on Antimicrobial Resistance. Antimicrobial Resistance: Tackling a Crisis for the Health and Wealth of Nations. 2014). This number exceeds the number of cancer fatalities each year, and the associated economic loss is estimated at about 100 trillion dollars. WHO's global action plan against infection caused by antimicrobial-resistant bacteria (Global Action Plan on Antimicrobial Resistance. World Health Organization. 2015) requires urgent action to deal with a flurry of development of antimicrobial resistance. The document also describes how to reduce the incidence of infection, how to optimize the use of antimicrobials, and the importance in complying with the optimal use.

In the midst of growing threats caused by antimicrobial-resistant bacteria and viruses, metallic copper (hereinafter also simply referred to as "copper") and alloys thereof are attracting attention as new antimicrobial and antiviral materials. This is because materials' surfaces touched by human hands are confirmed to play an important role in preventing infection. A material surface is not only a source of infection due to bacteria attached to the surface from human hands but also a cause of horizontal transfer of antimicrobial-resistance genes due to coexistence of several types of bacteria. Therefore, not only new antimicrobial-resistant bacteria but also multiantimicrobial-resistant bacteria may be generated. In order to prevent the generation of such bacteria, continuous disinfection of materials surfaces is necessary, and copper and copper alloys have attracted attention as such materials. It is reported that a surface of copper and a copper alloy exhibits strong bactericidal actions which destroy bacteria attached to the surface and degrade DNA of the bacteria in about several tens of minutes to several hours. Due to the gene degradation, it is determined that copper and copper alloys do not cause horizontal transfer that generates new antimicrobial-resistant bacteria and that copper and copper alloys are effective against many types of pathogens such as viruses and fungi as well as bacteria.

Accordingly, introduction of copper and copper alloy products are promoted in medical institutions, nursing homes, and places where many people gather (such as nurseries and public transportation vehicles). For example, in a demonstration experiment in a hospital, Non Patent Literature 1 reports an 83% reduction in bioburden (the number of viable microbes in an environment), and Non Patent Literature 2 reports a 58% reduction in incidence of healthcare-acquired infections (HAI).

CITATION LIST

Non Patent Literature

Non Patent Literature 1: M. G. Schmidt, et al. Journal of Clinical Microbiology 50 (2012) 2217-2223
Non Patent Literature 2: C. D. Salgado, et al. Infection Control and Hospital Epidemiology 34 (2013) 479-486

SUMMARY OF INVENTION

Technical Problem

Impressively, as described in the aforementioned reported case, even though an 80% or more reduction in bioburden is determined, bioburden is not reduced to zero, and the incidence of HAI is reduced by about half. One possible reason is that it takes time to manifest antimicrobial actions on a surface of copper and a copper alloy. If the antimicrobial actions on the surface of the copper and the copper alloy are manifested in few minutes, or tens of seconds, or few seconds but not in few hours, it may be possible to diminish the risks of infectious diseases and the aforementioned horizontal transfer of antimicrobial-resistance genes.

The present invention has been made in light of the circumstances, and an object of the present invention is to provide a method that improves antimicrobial activity of copper or a copper alloy and enhances immediate effects of antimicrobial actions on a surface.

Solution to Problem

In order to achieve the object, the present inventors have paid attention to reactive oxygen species, one of the mechanisms for manifesting antimicrobial actions of copper and a copper alloy.

Reactive oxygen species are considered to be generated in the living body by the Fenton reaction. The Fenton reaction is a reaction in which iron (II) ions and hydrogen peroxide ($H_2O_2$) are combined in an aqueous solution to generate hydroxyl radicals (—OH). It is known that a similar reaction occurs with copper (I) ions. A mechanism for generating hydrogen peroxide on a surface of copper and a copper alloy has yet to be revealed. However, hitherto, 0.5 to 2.0 mg/L of hydrogen peroxide is generated in 10 to 20 minutes after a contact of a LB-medium with seeded *Escherichia coli* to a surface of pure copper (Shigetoshi Kobuchi et al. have reported in Zairyo-to-Kankyo/Corrosion Engineering of Japan, 52 (2003), pp. 428-435). In the same document, a slight amount of hydrogen peroxide is generated by a contact of a similar LB-medium to a surface of pure silver, but not in case of gold. Furthermore, they have reported no generation of hydrogen peroxide by a contact of a simple LB-medium to a surface of pure copper.

It is also considered that copper (II) ions eluted from a surface of copper and a copper alloy have something to do with bactericidal actions on the surface of copper and the copper alloy (for example, G. Grass et al. Appln. Environ Microbiol. 77 (2011) 1541-1547). Specifically, the following mechanisms have been inferred which potentially act independently or interact with each other; A) copper (II) ions eluted from a surface of copper or a copper alloy damage bacterial cells in contact with the surface; B) the copper (II)

ions (and other stress-inducing events) destroy cellular membranes, causing loss of membrane potential and loss of cytoplasmic components; C) the copper (II) ions induce generation of hydroxyl radicals and reactive oxygen species, causing further damage to the cells; D) the bacteria damaged by the copper (II) ions decays, resulting in degradation of genomic DNA and plasmid DNA. There are still unclear points in these mechanisms of action. For example, microbes have important metabolic enzymes in cell walls, which are easily interact with extracellular copper (II) ions.

As described above, on a surface of copper and a copper alloy, bactericidal and antimicrobial actions are manifested by additive and synergistic effects of both elution of copper (II) ions and generation of hydrogen peroxide. Such findings give the present inventors an idea that promoting generation of hydrogen peroxide and elution of copper (II) ions on a surface of copper and a copper alloy enables a faster time to manifest bactericidal actions on the surface. As a result of intensive studies on substances and methods that exhibit such functions, the present inventors have found that treatment of a surface of copper or a copper alloy with a reducing substance in vivo (hereinafter referred to as "biological reducing substance") effectively generates hydrogen peroxide on the surface and that reactions between hydrogen peroxide and copper (I) ions on the surface of the copper or the copper alloy promotes generation of reactive oxygen species, which enhances manifesting efficiency of antimicrobial actions.

The findings of the present inventors are based on the thought that the aforementioned relation between reactive oxygen species, hydrogen peroxide, copper (I) ions, and copper (II) ions is represented by the following chemical equations (1) to (3) associated with actions of a reducing agent:

$$2Cu^{2+}+2RSH \rightarrow 2Cu^{+}+RSSR+2H^{+} \quad (1)$$

$$2Cu^{+}+2H^{+}+O_2 \rightarrow 2Cu^{2+}+H_2O_2 \quad (2)$$

$$Cu^{+}+H_2O_2 \rightarrow Cu^{2+}+OH^{-}+\cdot OH \quad (3)$$

(In Formula (1), RSH is a reducing agent, and RSSR is an oxidant of the reducing agent. Although thiol RSH is described as the reducing agent, note that thiol RSH is a typical example of the biological reducing substance. There is no intention to exclude reducing agents other than thiol-based substances).

Here, with regard to the bactericidal actions caused by Formulae (1) to (3), reactive oxygen species is principally generated even in an aqueous solution if copper ions and an appropriate reducing agent are involved. However, in order to generate a sufficient amount of reactive oxygen species for sterilization, copper ions at a fairly-high concentration are required. In addition, since reactive oxygen species has a short lifetime and moves in a very short distance, reactive oxygen species is effective only around the place where it is generated. Therefore, the fact that a region near a surface of an article made of copper or a copper alloy contains eluted ions at a higher concentration than that in a copper ion-containing liquid, or the fact that the surface of the article includes copper oxide (Cu₂O) that proceeds the aforementioned reactions on the surface, as described later, enables efficient sterilization.

Based on these new findings, the present inventors have made further studies and resulted in the present invention.

In an aspect of the present invention, there is provided a surface treatment method for copper or a copper alloy, in which the method comprises preparing a reducing agent solution containing a biological reducing substance, and treating a surface of copper or a copper alloy with the reducing agent solution.

Here, the copper or the copper alloy may be a wrought copper and copper alloy product.

The copper or the copper alloy may be a fiber, a particle, or foil of copper or a copper alloy contained in a porous body.

The porous body may be a woven fabric, a non-woven fabric, or a sponge.

Further, the treating may be performed at a relative humidity of 70% RH or less.

The copper or the copper alloy may be a Cu—Zn alloy, a Cu—Ni—Zn alloy, a Cu—Sn—Ni—Zn alloy, or a Cu—Si—Pb—P—Zn alloy.

The biological reducing substance may be at least one of reduced glutathione, N-acetylcysteine, sodium ascorbate, sodium sulfite, and cysteine.

The biological reducing substance may be reduced glutathione, and the reduced glutathione in the reducing agent solution may have a concentration of be 0.5 to 2.0 mM.

The copper or the copper alloy may include an oxide layer, and the oxide layer may contain 80.0% or more of Cu₂O and 20.0% or less of CuO in an area from the surface of the oxide layer to 1 μm measured by XPS.

In another aspect of the present invention, there is provided a surface treatment liquid for sterilizing copper or a copper alloy, in which the surface treatment liquid contains a biological reducing substance.

Here, the biological reducing substance may be at least one of reduced glutathione, N-acetylcysteine, sodium ascorbate, sodium sulfite, and cysteine.

In another aspect of the present invention, there is provided a sterilization method that comprises bringing copper or a copper alloy treated by the surface treatment method into contact with a surface of an object to sterilize the surface of the object.

Here, the copper or the copper alloy may be a fiber, a particle, or foil of copper or a copper alloy contained in a porous body.

The porous body may be a woven fabric, a non-woven fabric, or a sponge.

Advantageous Effects of Invention

According to the present invention, there is provided a surface treatment method that improves antimicrobial activity of copper or a copper alloy and enhances immediate effects of antimicrobial actions on the surface of the copper or the copper alloy.

Further, according to the present invention, there is provided a surface treatment liquid for sterilizing copper or a copper alloy, in which the surface treatment liquid contains a biological reducing substance.

Furthermore, according to the present invention, there is provided a sterilization method using copper or a copper alloy treated by the aforementioned method.

DESCRIPTION OF EMBODIMENTS

Figure 1:
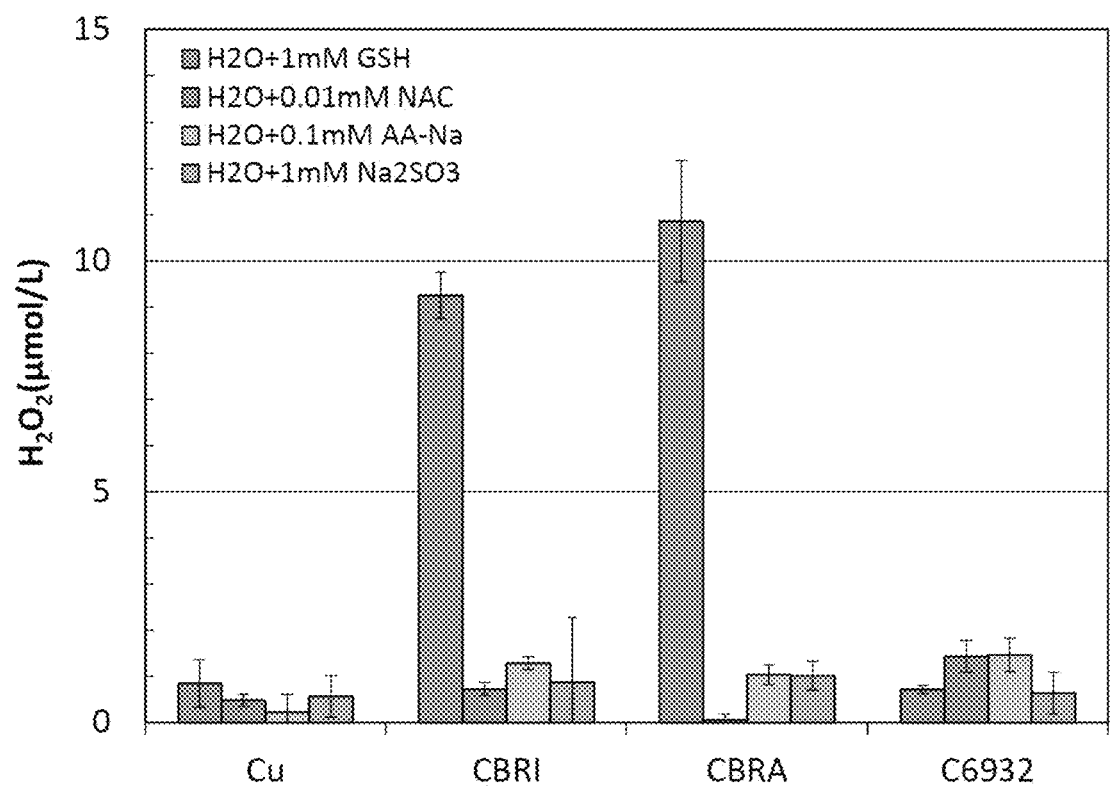
FIG. 1 shows results of hydrogen peroxide (H₂O₂) generation amounts measured in Example 1 by immersing sample pieces of Cu, CBRI, CBRA, and C6932 in reducing agent solutions containing different biological reducing substances.

Hereinafter, embodiments of the present invention will be described.

A surface treatment method for copper or a copper alloy according to an embodiment of the present invention comprises preparing a reducing agent solution containing a biological reducing substance, and treating a surface of copper or a copper alloy with the reducing agent solution.

In the surface treatment method according to this embodiment, first, a reducing agent solution containing a biological reducing substance is prepared.

The biological reducing substance is not particularly limited as long as it functions as a reducing agent (for example, RSH) in the chemical equation (1). Specific examples of the biological reducing substance include, but are not limited to, reduced glutathione (GSH), N-acetylcysteine (NAC), sodium ascorbate (AA-Na), sodium sulfite ($Na_2SO_3$), and cysteine (Cys).

A solvent for preparing the reducing agent solution is not particularly limited as long as it dissolves or suspends the biological reducing substance. Specific examples of the solvent include water ($H_2O$) and organic solvents but are not limited thereto. Note that the reducing agent solution may be a homogeneous solution containing a biological reducing substance completely dissolved in a solvent or may be a heterogeneous solution containing a biological reducing substance dispersed in a solvent.

A concentration of the biological reducing substance in the reducing agent solution is appropriately adjusted according to, for example, types of the biological reducing substance and solvent, and types of the copper or the copper alloy to be treated. For example, a reducing agent solution is prepared by adding a predetermined biological reducing substance, to a predetermined solvent, within a range of 0.01 to 10.0 mM, 0.05 to 7.5 mM, 0.1 to 5.0 mM, 0.5 to 2.0 mM, or 0.75 to 1.5 mM. Note that any additives may be added in the reducing agent solution as needed.

In the surface treatment method according to this embodiment, next, the surface of the copper or the copper alloy is treated with the reducing agent solution.

Examples of the copper used in this embodiment include, but are not limited to, copper having purity of 95% by mass or more, more preferably 99.90% by mass or more, such as oxygen-free copper (JIS H3100, alloy number C1020), tough pitch copper (JIS H3100, alloy number C1100), and phosphorous-deoxidized copper (JIS H3100, alloy numbers C1201 and C1220) specified in JIS H0500 and JIS H3100, and electrolytic copper foil.

In this specification, copper alloys represent alloys containing 50% by mass or more of copper. Examples of the copper alloys used in this embodiment include, but are not limited to, copper-zinc alloys (brass), copper-nickel alloys (cupronickel), copper-nickel-zinc alloys (nickel silver), copper-tin alloys (bronze), and copper-tin-phosphorus alloys (phosphor bronze).

In addition, as the copper alloys, for example, it is possible to use binary alloys having two basic component elements including copper, ternary alloys having three basic component elements including copper, and alloys having four or more basic component elements including copper. Examples of the binary alloys include Cu—Zn alloys, specifically, brass (JIS H3100, alloy numbers C2600 and C2680). Examples of the ternary alloys include Cu—Ni—Zn alloys. The ternary alloys preferably contain 50.0 to 60.0% by mass of Cu, 5.0 to 15.0% by mass of Ni, with the balance being zinc and inevitable impurities. Examples of the copper alloys having four or more basic component elements include Cu—Sn—Ni—Zn alloys and Cu—Si—Pb—P—Zn alloys. Preferably, Cu—Sn—Ni—Zn alloys contain 60.0 to 80.0% by mass of Cu, 0.1 to 1.0% by mass of Sn, 0.5 to 5.0% by mass of Ni, with the balance being zinc and inevitable impurities. Preferably, Cu—Si—Pb—P—Zn alloys contain 65.0 to 85.0% by mass of Cu, 1.0 to 5.0% by mass of Si, 0.01 to 1.0% by mass of Pb, 0.01 to 0.5% by mass of P, with the balance being zinc and inevitable impurities.

Taking various conditions into account such as types, sizes, and shapes of copper or a copper alloy to be treated, various known modes such as spraying, coating, and immersion may be appropriately selected as a mode for surface treatment of copper or a copper alloy with a reducing agent solution.

The surface treatment of copper or a copper alloy with a reducing agent solution is preferably performed while a surface of copper or a copper alloy to be treated is dry. For example, the surface treatment of copper or a copper alloy with a reducing agent solution is performed in the atmosphere in which a temperature is controlled to 30° C. or less and a relative humidity is controlled to 70% RH or less. However, even though a temperature is higher than 30° C. or a relative humidity is higher than 70% RH, it is possible to obtain effects of the present invention.

On a surface of copper or a copper alloy treated with a reducing agent solution, a biological reducing substance contained in the reducing agent solution reacts with copper (II) ions eluted from the surface, and this reaction proceeds the chemical equation (1) and generates copper (I) ions. This reaction promotes generation of copper (II) ions and hydrogen peroxide ($H_2O_2$) by the chemical equation (2) and generation of copper (II) ions and hydroxyl radicals (—OH)

by the chemical equation (3). Furthermore, the copper (II) ions generated by the chemical equation (2) or the chemical equation (3) cause another reaction with the biological reducing substance by the chemical equation (1). Accordingly, compared with a surface of untreated copper or an untreated copper alloy, the surface of the copper or the copper alloy is provided with more copper (II) ions, hydrogen peroxide, and hydroxyl radicals, which enhances immediate effects of antimicrobial actions on the surface and increases manifesting efficiency of the antimicrobial actions of the copper or copper alloy. Such a mechanism of action is inferred with a certain reliability based on the results of the following Examples.

In view of the mechanism of action, in this embodiment, it is considered that creating a state with copper (I) present on a surface of copper or a copper alloy is effective in increasing immediate effects of antimicrobial actions on the surface. This is because copper (II) ions, hydrogen peroxide, and hydroxyl radicals may be generated by the chemical equations (2) and (3) on a surface with copper (I). Generally, copper and copper alloys gradually discolor due to an oxide layer formed on a surface thereof in a normal usage environment. Therefore, as a preliminary test, the present inventors exposed a sample of oxygen-free copper (C1020) to the normal atmosphere for three months and conducted XPS analysis on the surface of the sample. According to the result, a proportion of $Cu_2O$ and $CuO$ was 83.0% and 17.0%, respectively.

The surface treatment method according to this embodiment is effectively applied to copper or a copper alloy having a polished surface, and applied to copper and a copper alloy having an oxide layer on the surface thereof and containing a high proportion of $Cu_2O$ in elemental compositions determined by XPS analysis. An example of the oxide layer includes one that contains 80.0% or more of $Cu_2O$ and 20.0% or less of $CuO$ in an area from the surface of the oxide layer to 1 μm measured by XPS. In addition, the oxide layer is not limited to those formed by exposure to the atmosphere and may be formed, for example, by treating a surface of copper or a copper alloy by any generally applicable method.

In this manner, on a surface of copper or a copper alloy having an oxide layer containing a large amount of $Cu_2O$, copper (II) ions are eluted from the surface of the metal copper or the copper alloy into the aforementioned reducing agent solution. The elution of the copper (II) ions initiates and proceeds reactions represented by the chemical equations (1) to (3). In addition, the presence of more copper (I) on the surface of the copper or the copper alloy results in more copper (II) ions, hydrogen peroxide, and hydroxyl radicals. Accordingly, immediate effects of antimicrobial actions on the surface are further enhanced, leading to an increase in manifesting efficiency of the antimicrobial actions of the copper or the copper alloy. Such a mechanism of action is inferred with a certain reliability based on the results of the following Examples.

Furthermore, in a more specific aspect of this embodiment, the copper or the copper alloy is preferably a wrought copper and copper alloy product. In this specification, the wrought copper and copper alloy product is a general term for products such as sheets, strips, tubes, rods, and wires of copper and copper alloys produced by hot or cold plastic working such as rolling, extrusion, drawing, and forging according to the definition specified in JIS H0500. Treatment of a surface of such a wrought copper and copper alloy product with the reducing agent solution of this embodiment enables quick and efficient destruction of bacteria, microbes and the like attached to the surface and sterilizes the surface. The wrought copper and copper alloy product to which the surface treatment method according to this embodiment is applied is not limited to those used independently and may be used in combination with other products. Examples of the wrought copper and copper alloy product include, but are not limited to, articles, equipment, components, and indoor floors and wall surfaces, in which copper or a copper alloy is used in whole or in part. More specifically, the surface treatment method according to this embodiment is effectively applied to members used in environments that require eradication, sterilization, and disinfection, such as kitchen sinks, bathroom walls, medical institutions, nursing homes, and floors and walls of pharmaceutical and medical equipment manufacturing facilities.

In another specific aspect, the copper or the copper alloy is preferably a fiber, a fine particle, or foil of copper or a copper alloy (hereinafter simply represented by a copper fiber) contained in a woven fabric, a non-woven fabric, a sponge, or other general flexible porous materials (hereinafter represented by a cloth). In this case, the reducing agent solution of this embodiment is applied to the cloth to treat the surface of the copper fiber with the reducing agent solution. The sterilized cloth damp with the reducing agent solution is brought into contact with a surface of an object (for example, dry or wipe the surface) so as to transfer bacteria, microbes, and the like attached to the surface of the object to the surface of the sterilized cloth and remove those bacteria and the like from the surface. Furthermore, reactive oxygen species and eluted copper ions generated around the copper fiber quickly and efficiently destroy bacteria, microbes, and the like. Accordingly, the surface of the object is sterilized.

In this manner, the reducing agent solution according to this embodiment is preferably used for the surface treatment of copper or a copper alloy. In other words, the reducing agent solution according to this embodiment is preferably used as a surface treatment liquid for sterilizing copper or a copper alloy.

Furthermore, when copper or a copper alloy treated by the surface treatment method according to this embodiment is brought into contact with a surface of an object, it is possible to sterilize the surface of the object.

EXAMPLES

Hereinafter, the present invention will be described in more detail with reference to Examples, but the present invention is not limited to the following Examples.

[Copper and Copper Alloy Samples]

The following samples were used as copper and copper alloy samples:

Oxygen-free copper (alloy number C1020. Also referred to "C1020" or "Cu".)

Brass (alloy number C2680. Also referred to "C2680".)

Clean Bright (registered trademark) (Mitsubishi Shindoh Co., Ltd. Also referred to "CBRI".) Typical composition: 54.0 Cu-11.0 Ni—Zn (% by mass)

Clean Brass (registered trademark) (Mitsubishi Shindoh Co., Ltd. Also referred to "CBRA".) Typical composition: 70.0 Cu-0.5 Sn-2.0 Ni—Zn (% by mass)

Eco Brass (registered trademark) (Mitsubishi Shindoh Co., Ltd. Also referred to "C6932".) Typical composition: 75.5 Cu-3.0 Si-0.09 Pb-0.1 P—Zn (% by mass)

Unless otherwise described in the following Examples, copper and copper alloy samples have no oxide layer on the surface thereof or have an oxide layer (natural oxide layer) to a negligible extent.

Example 1

Reduced glutathione (GSH), N-acetylcysteine (NAC), sodium ascorbate (AA-Na), sodium sulfite ($Na_2SO_3$), and cysteine (Cys) were used as biological reducing substances. Reducing agent solutions were prepared by adding each biological reducing substance to water ($H_2O$) in a concentration range in which the biological reducing substance is dissolved.

Each sample piece (Cu, CBRI, CBRA, and C6932) having a surface area of 0.95 cm$^2$ was immersed in each reducing agent solution for 24±1 hours, and then, each hydrogen peroxide ($H_2O_2$) generation amount was measured.

The $H_2O_2$ generation amount was calculated based on a difference from the time of adding $H_2O_2$ scavenger (catalase) by the xylenol orange (XO) method and shown as a generation amount per unit solution. The following Examples are carried out in similar conditions.

Figure 2:
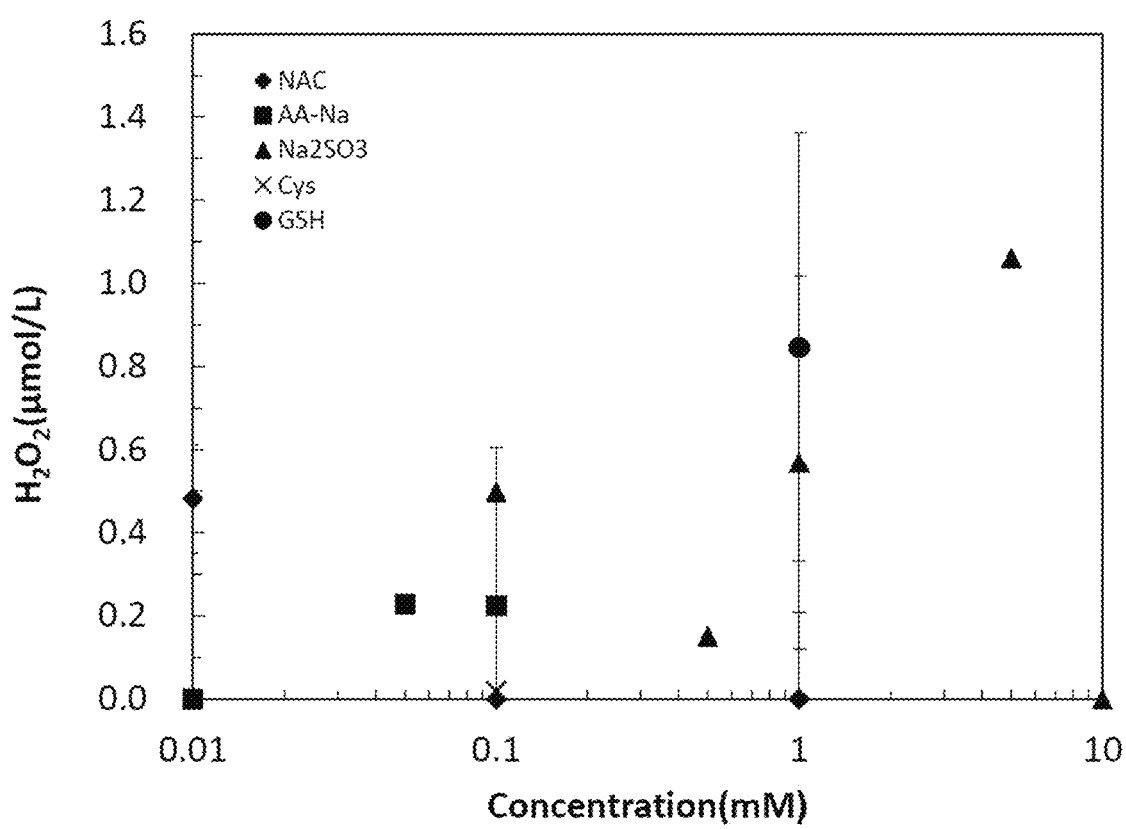
FIG. 2 shows results of hydrogen peroxide (H₂O₂) generation amounts measured in Example 1 by immersing a Cu sample piece in reducing agent solutions containing different biological reducing substances.

Results are shown in FIGS. 1 and 2.

FIG. 1 shows the results of immersion tests on sample pieces of Cu, CBRI, CBRA, and C6932. Reducing agent solutions of 1 mM GSH, 0.01 mM NAC, 0.1 mM AA-Na, and 1.0 mM $Na_2SO_3$ were used in the immersion tests for each sample piece, and the results are shown in this order from the left.

FIG. 2 shows the results of immersion tests on Cu using reducing agent solutions of NAC (0.01 mM, 0.1 mM, 1.0 mM), AA-Na (0.01 mM, 0.05 mM, 0.1 mM), $Na_2SO_3$ (0.1 mM, 0.5 mM, 1.0 mM, 5.0 mM, 10.0 mM), Cys (0.1 mM), and GSH (1.0 mM).

These results show that, with any reducing substance, $H_2O_2$ was generated from the samples. Particularly, when using a GSH solution, a certain amount of $H_2O_2$ was generated in each sample, and $H_2O_2$ generation amounts in CBRI and CBRA were prominent. Accordingly, GSH was adopted as a biological reducing substance in Example 2 and in subsequent Examples.

In this Example, reducing agent solutions containing one type of biological reducing substance were used. For example, when a solution of Cys (0.1 mM) was used, a very small amount of $H_2O_2$ was generated. However, it should be noted that $H_2O_2$ generation amount may be increased in different concentration conditions or by combining with other biological reducing substances.

Example 2

In this Example, a relation between a GSH concentration in a reducing agent solution and a $H_2O_2$ generation amount was studied.

GSH was added to water ($H_2O$) at a concentration of 0.1 mM, 0.5 mM, and 1.0 mM to prepare reducing agent solutions. As in Example 1, immersion tests were performed on Cu, C2680, CBRI, and CBRA, and each $H_2O_2$ generation amount was measured.

For comparison, a similar immersion test was performed using a 500-fold diluted nutrient broth (1/500 NB) under conditions based on the test for antimicrobial activity specified in JIS Z2801.

Figure 3:
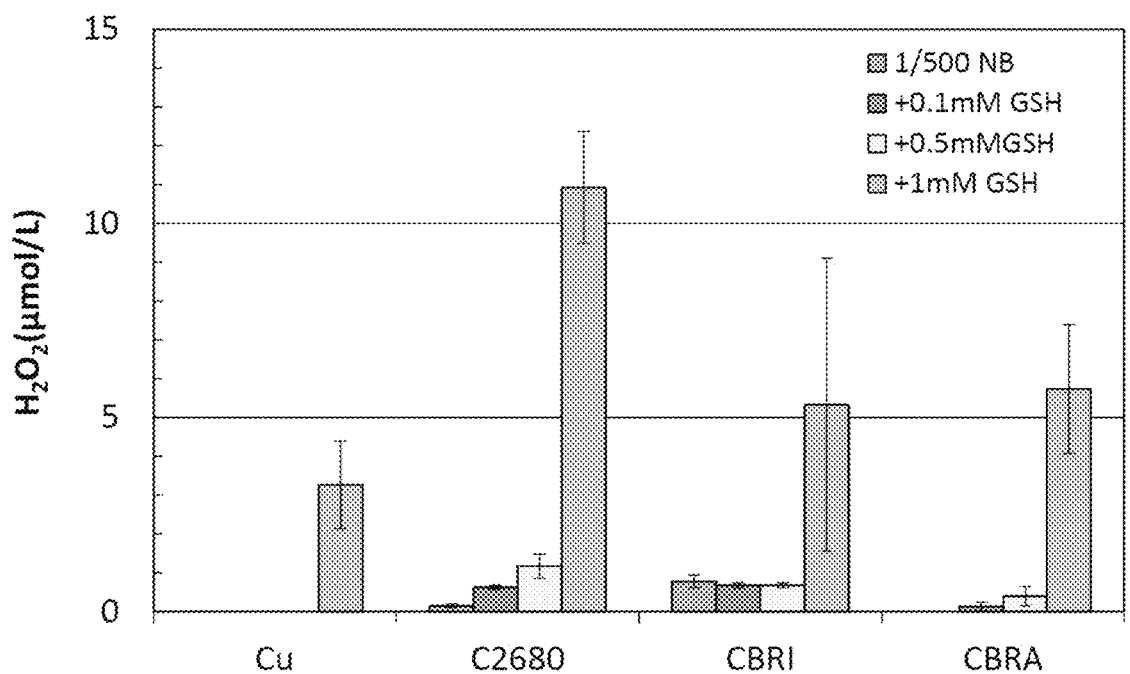
FIG. 3 shows results of hydrogen peroxide ($H_2O_2$) generation amounts measured in Example 2 by immersing sample pieces of Cu, C2680, CBRI, and CBRA in reducing agent solutions containing GSH having different concentrations.

Results are shown in FIG. 3.

FIG. 3 shows the results of the immersion tests on sample pieces of Cu, C2680, CBRI, and CBRA. Reducing agent solutions of 1/500 NB, 0.1 mM GSH, 0.5 mM GSH, and 1.0 mM GSH were used in the immersion tests for each sample piece, and the results are shown in this order from the left.

In each sample piece, when a GSH concentration was 0.1 mM, a $H_2O_2$ generation amount was very small. The results also show that a $H_2O_2$ generation amount increases depending on a GSH concentration. Particularly, when a GSH concentration was 1.0 mM, an increase in $H_2O_2$ generation amount was prominent compared with cases where GSH concentrations were 0.1 mM and 0.5 mM.

Example 3

In this Example, a GSH concentration was fixed at 1.0 mM, and a relation between a solvent of a reducing agent solution and a $H_2O_2$ generation amount was studied.

GSH was added at a concentration of 1.0 mM to 500-fold diluted nutrient broth (1/500 NB), water ($H_2O$), 0.9% NaCl, and 5% NaCl to prepare reducing agent solutions. As in Example 1, immersion tests were performed on Cu, C2680, C6932, CBRI, and CBRA, and each $H_2O_2$ generation amount was measured.

Figure 4:
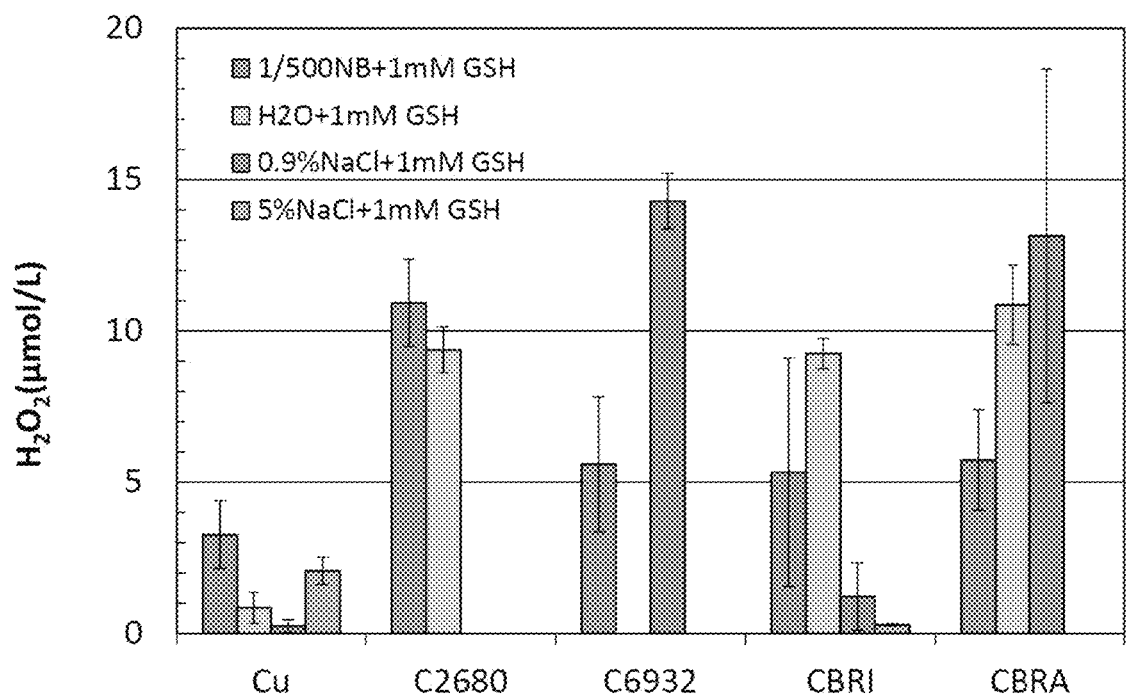
FIG. 4 shows results of hydrogen peroxide ($H_2O_2$) generation amounts measured in Example 3 by immersing sample pieces of Cu, C2680, C6932, CBRI, and CBRA in reducing agent solutions containing different solvents to which GSH was added at a concentration of 1.0 mM.

Results are shown in FIG. 4.

FIG. 4 shows the results of the immersion tests on sample pieces of Cu, C2680, C6932, CBRI, and CBRA. Reducing agent solutions in which GSH was added at a concentration of 1.0 mM to 1/500 NB, $H_2O$, 0.9% NaCl, and 5% NaCl were used in the immersion tests for each sample piece, and the results are shown in this order from the left.

These results indicate that a solvent contained in a reducing agent solution is appropriately selected according to, for example, types of copper or copper alloys, types of biological reducing substances, and concentrations of biological reducing substances in the reducing agent solution.

Example 4

In this Example, a reducing agent solution containing 1.0 mM GSH was used, and $H_2O_2$ generation amounts in various copper and copper alloy samples were measured.

As a condition based on the test for antimicrobial activity specified in JIS Z2801, GSH was added at a concentration of 1.0 mM to 5 mL of 500-fold diluted nutrient broth (1/500 NB), whereby preparing a reducing agent solution. Immersion tests were performed in a similar manner to Example 1 on Cu, C2680, C6932, CBRI, and CBRA and also on antimicrobial stainless steel (antimicrobial SS) and metallic silver (Ag) as samples for comparison. Then, each $H_2O_2$ generation amount was measured.

For comparison, each sample was subjected to a similar immersion test using 5 mL of 500-fold diluted nutrient broth (1/500 NB) without GSH.

Figure 5:
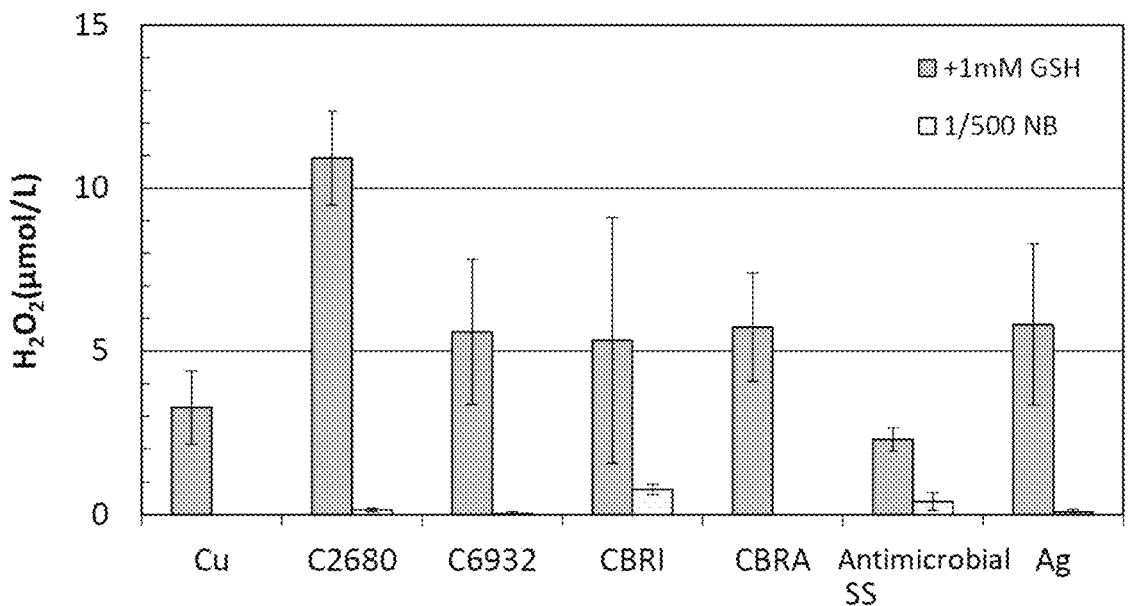
FIG. 5 shows results of hydrogen peroxide ($H_2O_2$) generation amounts measured in Example 4 by immersing sample pieces of Cu, C2680, C6932, CBRI, CBRA, antimicrobial SS, and Ag in reducing agent solutions to which GSH was added at a concentration of 1.0 mM.

Results are shown in FIG. 5.

FIG. 5 shows the results of the immersion tests on sample pieces of Cu, C2680, C6932, CBRI, CBRA, antimicrobial SS, and Ag. The bar graph on the left of each sample piece shows the result of the immersion test using 1/500 NB to which GSH was added at a concentration of 1.0 mM, and the bar graph on the right shows the result of the immersion test using 1/500 NB without GSH.

With the reducing agent solution of 1/500 NB to which GSH was added, $H_2O_2$ was generated from each sample. It was also determined that a $H_2O_2$ generation amount differs depending on types of samples.

Example 5

In this Example, effects of GSH, which is a biological reducing substance, on antimicrobial activity of copper and copper alloys were studied by a simple test for antimicrobial activity using *E. coli* based on the test for antimicrobial activity specified in JIS Z2801.

Figure 6:
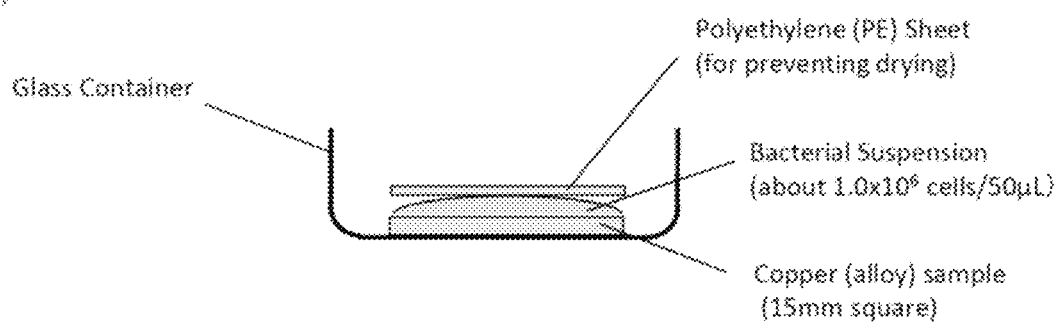
FIGS. 6(a) and 6(b) are schematic views showing an outline of a simple test for antimicrobial activity using *Escherichia coli* (*E. coli*) in Example 5.
Figure 6:
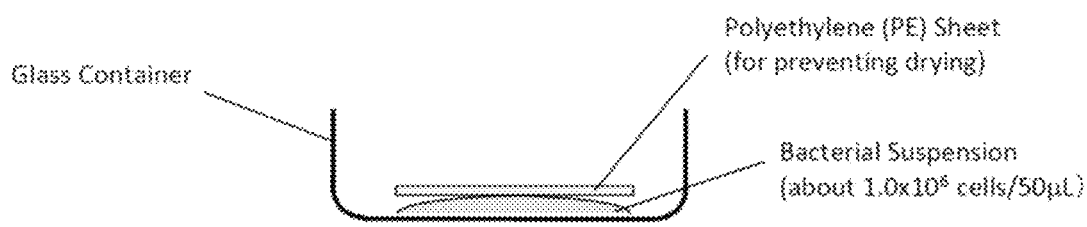

FIGS. 6(a) and 6(b) are schematic views showing an outline of the test for antimicrobial activity performed in this Example.

As shown in FIG. 6(a), first, a copper (Cu) sample piece (15 mm square) was placed on the bottom surface of a glass container. Next, on the upper surface of the sample piece, 0.9% NaCl (−GSH) not containing GSH as a solvent or a 0.9% NaCl solution (+GSH) containing GSH at a concentration of 1.0 mM as a solvent was used to seed about $1.0 \times 10^6$ cells/50 µL of *E. coli*. This bacterial suspension was covered with a polyethylene (PE) sheet so as not to dry the bacterial suspension. Then, the glass container was placed under static culture condition of 35±1° C. The PE sheet was removed 0 minute (immediately after seeding), 5 minutes, and 10 minutes after seeding of *E. coli*, and 1 mL of 0.9% NaCl+0.1 mM EDTA-2Na was added to the bacterial suspension, and the bacterial suspension was collected by pipetting. A fluorescent dye was added to the collected bacterial suspension, and viability of *E. coli* was determined by measuring fluorescence intensity. In order to avoid a contact between the back surface of the Cu sample piece and the solution when collecting *E. coli*, the back surface of the Cu sample piece was coated with a thin silicone sheet in advance.

As a control, as shown in FIG. 6(b), seeding of *E. coli* was performed in a similar manner to the above procedure except that a Cu sample piece was not placed on the bottom of a glass container, and viability of *E. coli* after 10 minutes from seeding was measured.

Figure 7:
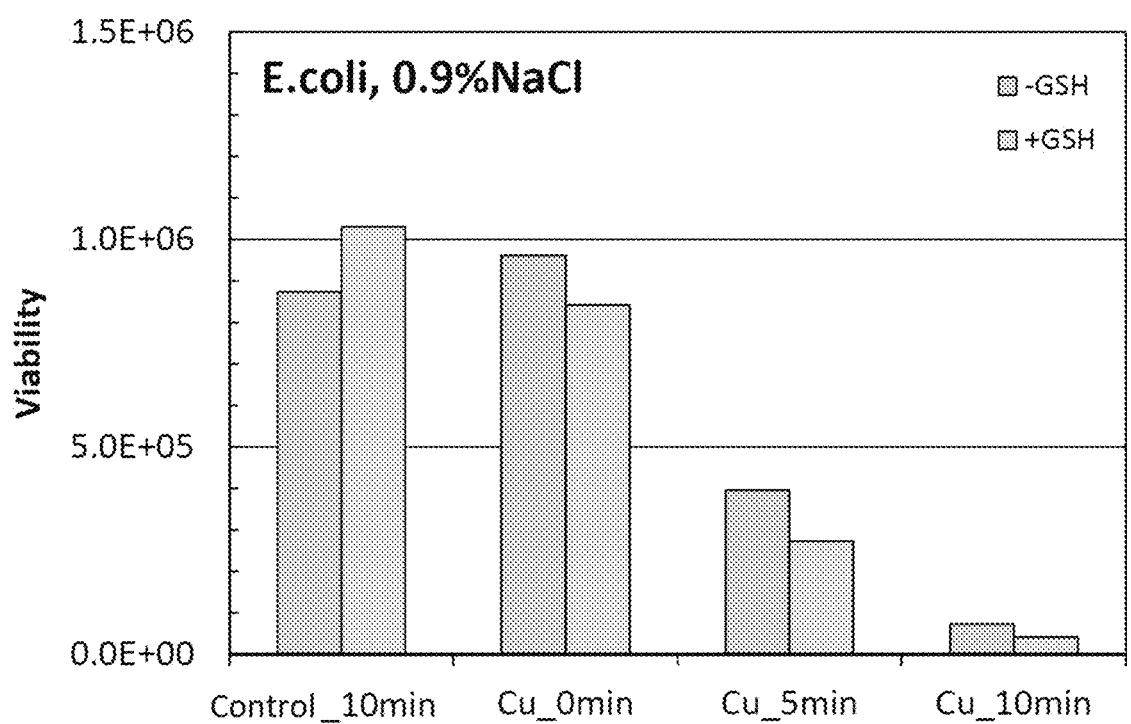
FIG. 7 shows results of the simple test for antimicrobial activity using *E. coli* in Example 5.

Results are shown in FIG. 7.

FIG. 7 shows the results of the viability of *E. coli* in the control (10 minutes after seeding), the Cu sample (0 minute; immediately after seeding), the Cu sample (5 minutes after seeding), and the Cu sample (10 minutes after seeding). The bar graph on the left of each sample piece shows the viability of *E. coli* when using the 0.9% NaCl (−GSH), and the bar graph on the right shows the viability of *E. coli* when using the 0.9% NaCl solution (+GSH) to which GSH was added at a concentration of 1.0 mM.

In the Cu sample immediately (0 minutes) after seeding of *E. coli*, viability of *E. coli* decreased due to the addition of GSH, but the viability was equivalent to the result of the control. On the other hand, in the Cu samples of 5 minutes and 10 minutes after seeding of *E. coli*, viability decreased due to the addition of GSH, and the viability decreased more than the result of the control. Particularly, the decrease of the viability 10 minutes after seeding was considerable.

Figure 8:
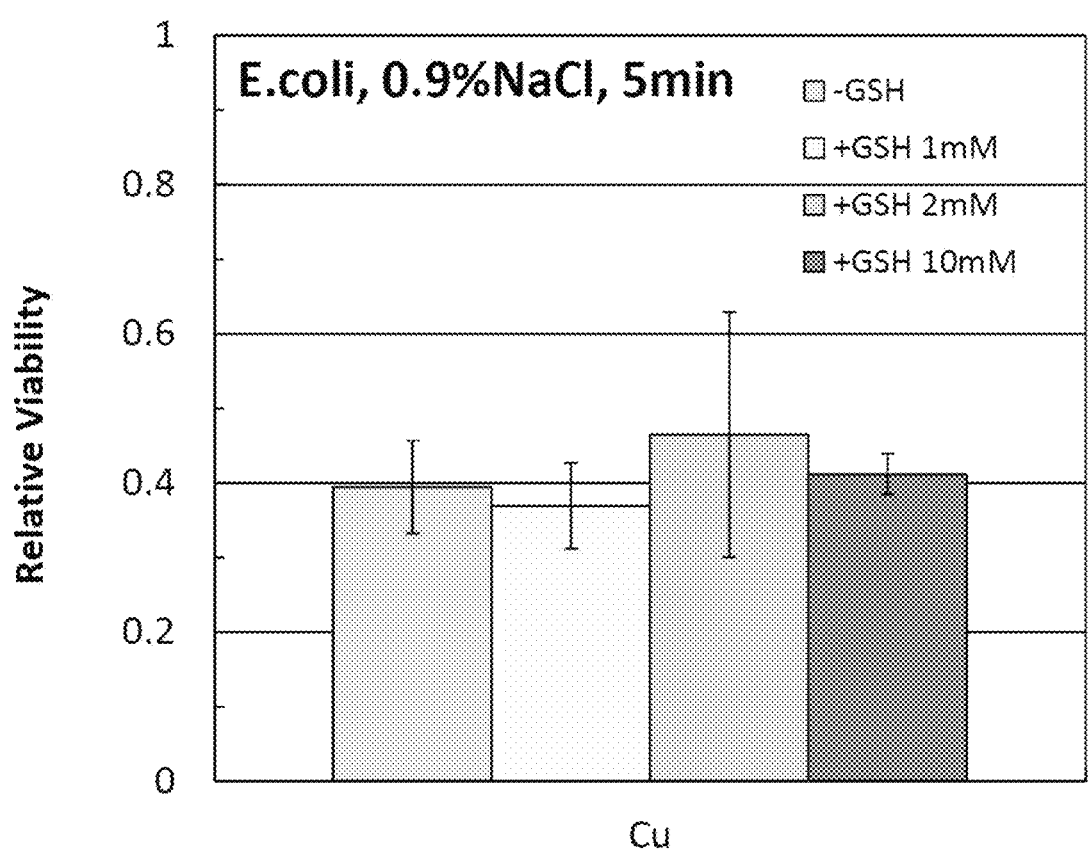
FIG. 8 shows results of the simple test for antimicrobial activity using *E. coli* in Example 5.

FIG. 8 shows results of viability of *E. coli* measured 5 minutes after seeding of *E. coli* on a surface of a Cu sample piece in a manner similar to the above procedure. GSH was added at a concentration of 0 mM (no addition), 1.0 mM, 2.0 mM, and 10.0 mM, and the results are shown in this order from the left. In FIG. 8, the longitudinal axis represents a ratio of bacterial viability (relative viability) normalized to the bacterial viability in the control test as 1.

As in FIG. 7, when a GSH concentration was 1.0 mM, bacterial viability decreased more than a case without GSH (0.9% NaCl). However, when GSH was added at a concentration of 2.0 mM or 10.0 mM, viability was equivalent or greater than the result without GSH (0.9% NaCl).

These results show that improvement in antimicrobial activity of copper and a copper alloy by GSH (biological reducing substance) depends on the amount of $Cu^{2+}$ eluted on the surface of the copper and the copper alloy and on physical and chemical states of the surface.

Example 6

In this Example, instead of Cu, CBRA was used as a copper alloy sample, and a simple test for antimicrobial activity using *E. coli* was performed in a similar manner to Example 5. Note that the time from seeding of *E. coli* to collection of a bacterial suspension was set to 5 minutes.

Figure 9:
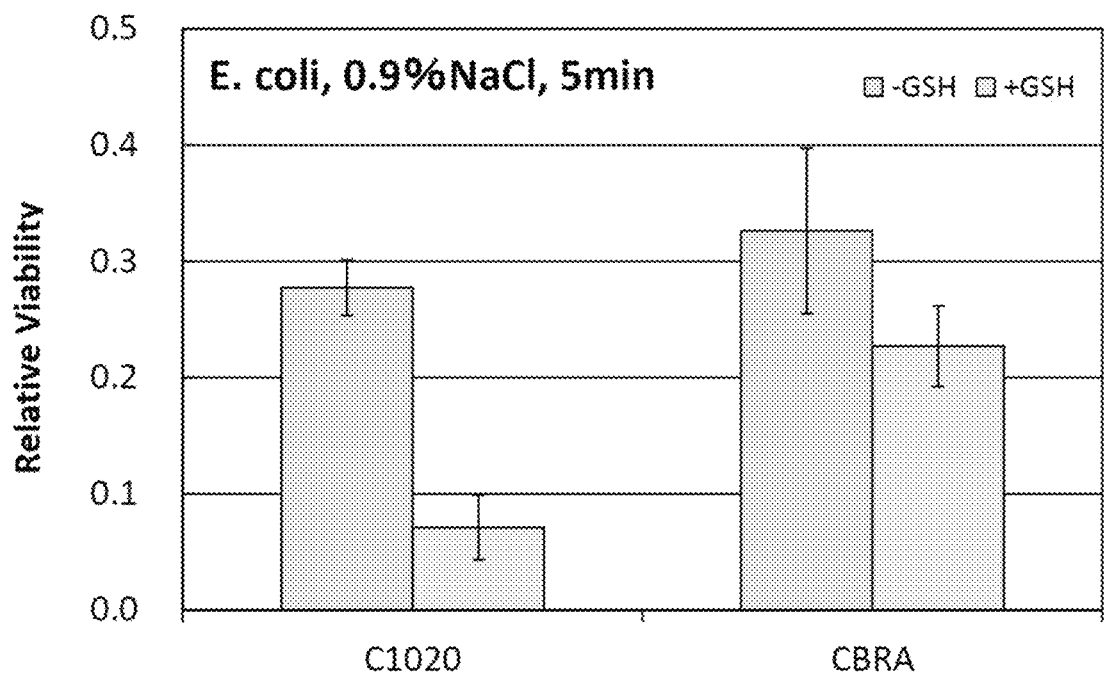
FIG. 9 shows results of a simple test for antimicrobial activity using *E. coli* in Example 6.

Results are shown in FIG. 9.

In FIG. 9, the bar graph on the left of each sample piece shows viability of *E. coli* when using 0.9% NaCl (−GSH), and the bar graph on the right shows viability of *E. coli* when using a 0.9% NaCl solution (+GSH) to which GSH was added at a concentration of 1.0 mM. In FIG. 9, the longitudinal axis represents a ratio of bacterial viability (relative viability) normalized to the bacterial viability in the control test as 1. FIG. 9 also shows the results using a Cu (C1020) sample piece for comparison.

In addition to Cu used in Example 5, the CBRA sample piece of this Example reduced in bacterial viability compared with the control test. The results also show that addition of GSH further decreased the viability. These results show that both copper and a copper alloy significantly improve in antimicrobial activity by GSH (biological reducing substance).

Example 7

In this Example, an antimicrobial activity test using *E. coli* based on the antimicrobial activity test specified in JIS Z2801 was performed in a similar manner to Example 5 except that a 500-fold diluted nutrient broth (1/500 NB) was used instead of 0.9% NaCl. Cu (C1020), CBRI, and C6932 were used as copper and copper alloy samples, and antimicrobial stainless steel (SS) and metallic silver (Ag) were used as samples for comparison.

Figure 10:
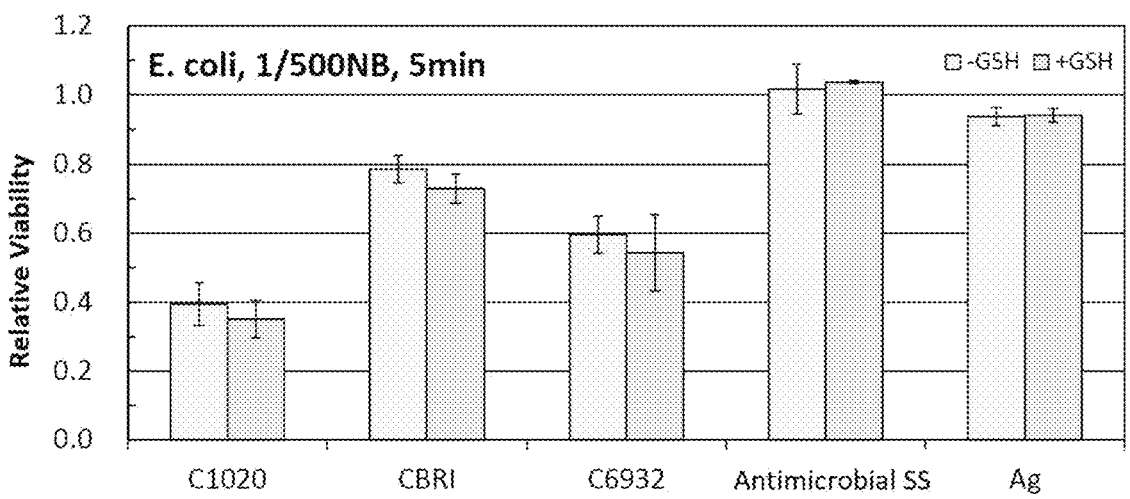
FIG. 10 shows results of a test for antimicrobial activity using *E. coli* in Example 7.

Results are shown in FIG. 10.

In FIG. 10, the bar graph on the left of each sample piece shows viability of *E. coli* when using 1/500 NB (−GSH), and the bar graph on the right shows viability of *E. coli* when using a 1/500 NB solution (+GSH) to which GSH was added at a concentration of 1.0 mM. In FIG. 10, the longitudinal axis represents a ratio of bacterial viability (relative viability) normalized to the bacterial viability in the control test as 1.

In each of the copper and copper alloy samples, the bacterial viability decreased more than the result of the control test, and the viability further decreased by addition of GSH. On the other hand, in the antimicrobial SS and Ag, the bacterial viability did not decrease by addition of GSH, and the viability did not decrease comparing to that in the control test.

Example 8

In this Example, an antimicrobial activity test based on the antimicrobial activity test specified in JIS Z2801 was performed in a similar manner to Example 7 except that *S. aureus* was used instead of *E. coli*. Cu (C1020), C6932, and C2680 were used as copper and copper alloy samples, and antimicrobial stainless steel (SS) and metallic silver (Ag) were used as samples for comparison.

Figure 11:
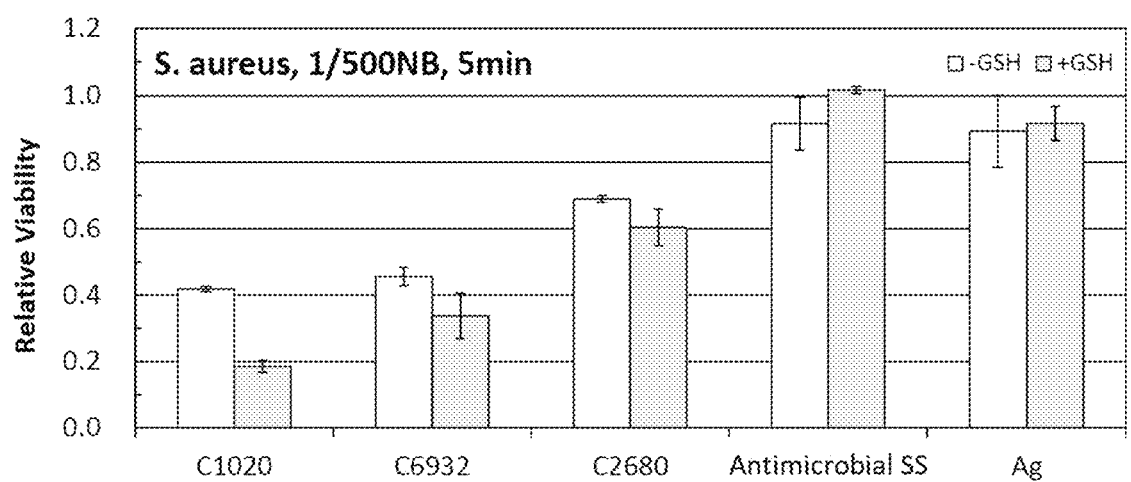
FIG. 11 shows results of a test for antimicrobial activity using *Staphylococcus aureus* (*S. aureus*) in Example 8.

Results are shown in FIG. 11.

In FIG. 11, the bar graph on the left of each sample piece shows the viability of *S. aureus* when using 1/500 NB (−GSH), and the bar graph on the right shows the viability of *S. aureus* when using 1/500 NB (+GSH) to which GSH was added at a concentration of 1.0 mM. In FIG. 11, the longitudinal axis represents a ratio of viability (relative viability) normalized to the viability in the control test as 1.

In each of the copper and copper alloy samples, bacterial viability decreased comparing to that in the control test, and the viability further decreased by addition of GSH. On the other hand, in the antimicrobial SS and Ag, the bacterial viability did not decrease by addition of GSH nor comparing to that in the control test.

Example 9

In this Example, antimicrobial activity tests using *E. coli* and *S. aureus* based on the antimicrobial activity test specified in JIS Z2801 were performed in a similar manner to Example 7 except that copper and copper alloy samples were exposed to the atmosphere for a certain period of time. Cu, CBRA, and C2680 were used as copper and copper alloy samples.

Figure 12:
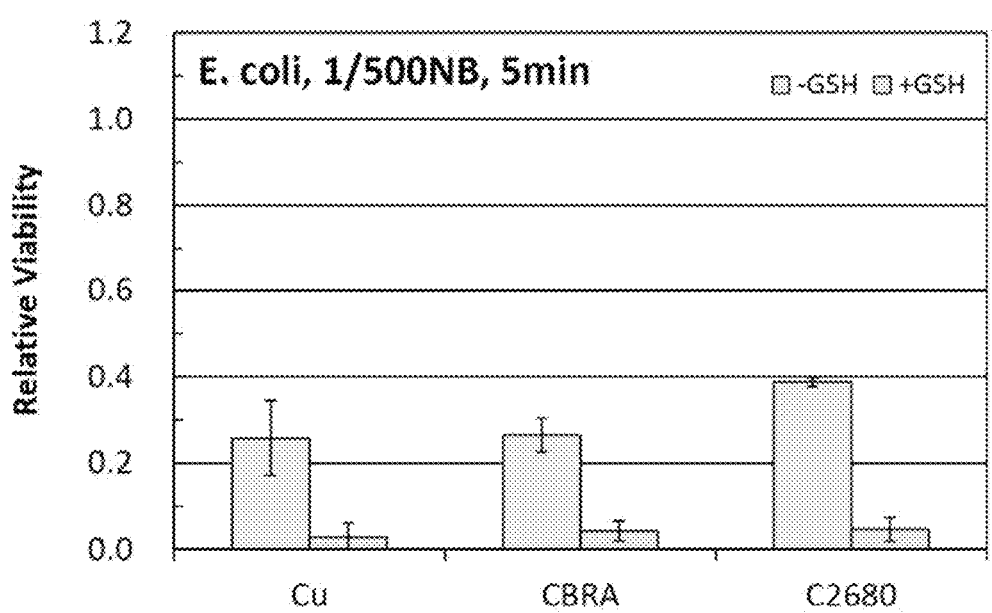
FIGS. 12(a) and 12(b) show results of a test for antimicrobial activity using *E. coli* and *S. aureus* in Example 9.
Figure 12:
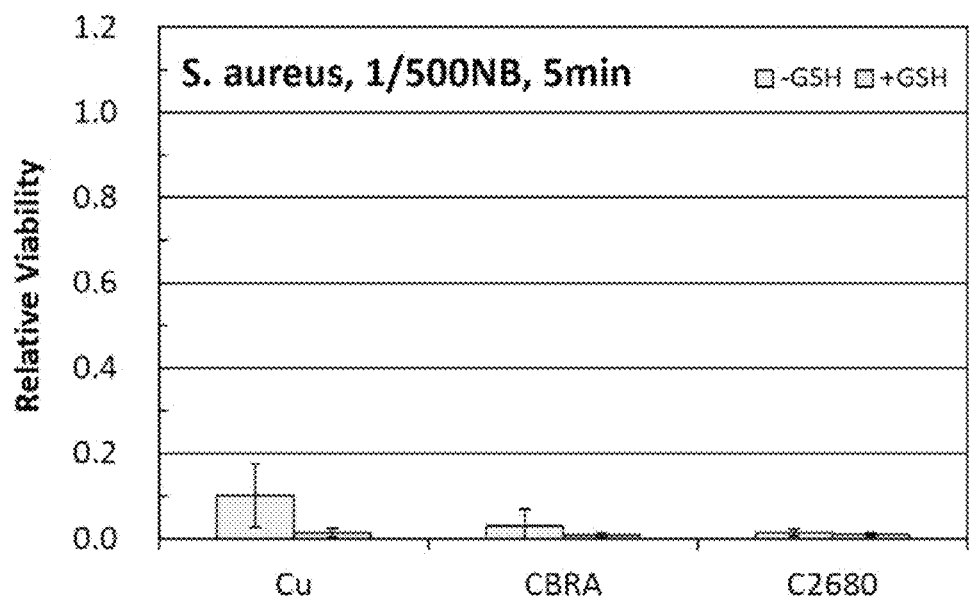

Results are shown in FIGS. 12(*a*) and 12(*b*).

In FIGS. 12(*a*) and 12(*b*), the bar graph on the left of each sample piece shows the viability of *E. coli* (FIG. 12(*a*)) or *S. aureus* (FIG. 12(*b*)) when using 1/500 NB NaCl (−GSH), and the bar graph on the right shows the viability of *E. coli* or *S. aureus* when using 1/500 NB (+GSH) to which GSH was added at a concentration of 1.0 mM. In FIGS. 12(*a*) and 12(*b*), the longitudinal axis represents a ratio of viability (relative viability) normalized to the bacterial viability in the control test as 1.

In each of the copper and copper alloy samples, the viability of *E. coli* and *S. aureus* decreased comparing to those in the control tests, and the viability further decreased by addition of GSH.

Although it is difficult to simply compare the results in this Example with the results in Example 7 (FIG. 10) and Example 8 (FIG. 11) because types (compositions) of the copper alloy samples are different, the effects on the exposed materials caused by addition of GSH were prominent in this Example. These results indicate that the effects of a reducing agent present on a surface of copper and a copper alloy and the effects of copper (I) act additively and synergistically so as to promote generation of reactive oxygen species, which accelerates the manifest of antimicrobial actions on the surface of the copper and the copper alloy and enhances their antimicrobial activity.

With regard to the exposed materials of Cu, CBRA, and C2680 used in this Example, surfaces of the samples were exposed in the atmosphere for three months, and the surfaces were analyzed by XPS. The analysis shows that the proportions of $Cu_2O$ in Cu, CBRA, and C2680 were 83.0%, 90.0%, and 92.9%, respectively. For comparison, a proportion of $Cu_2O$ on an exposed CBRI surface was measured under similar conditions, and the result was 84.6%. As described above, the surface of exposed materials contains $Cu_2O$ in a higher proportion than CuO, which indicates the presence of copper (I) in addition to copper (II) ions has significant contributions. This indicates that, in addition to the effects of a biological reducing substance, the presence of copper (I) on a surface of copper or a copper alloy may be a promising factor for improving antimicrobial activity of the copper or the copper alloy. This is one of analytical data that supports the findings of the present inventors.

The embodiments of the present invention have been described in detail. However, specific embodiments are not limited to these embodiments, and any modification in design within the gist of the present is included in the present invention.

The invention claimed is:

1. A surface treatment method for articles, equipment, components, indoor floors, or wall surfaces, in which copper or a copper alloy is used in whole or in part, the method comprising:
    preparing a reducing agent solution containing a biological reducing substance, the biological reducing substance being at least one selected from the group consisting of reduced glutathione, N-acetylcysteine, sodium ascorbate, sodium sulfite, and cysteine, and
    treating the surface of the articles, the equipment, the components, the indoor floors, or the wall surfaces with the reducing agent solution.

2. The surface treatment method according to claim 1, wherein the copper or the copper alloy is a wrought copper and copper alloy product.

3. The surface treatment method according to claim 1, wherein the treating is performed on the surface of the article, in which copper or a copper alloy is used in whole or in part,
    the article is a porous body, and
    the copper or the copper alloy is a fiber, a particle, or foil of copper or a copper alloy contained in the porous body.

4. The surface treatment method according to claim 3, wherein the porous body is a woven fabric, a non-woven fabric, or a sponge.

5. The surface treatment method according to claim 1, wherein the treating is performed at a relative humidity of 70% RH or less.

6. The surface treatment method according to claim 1, wherein the copper or the copper alloy is a Cu—Zn alloy, a Cu—Ni—Zn alloy, a Cu—Sn—Ni—Zn alloy, or a Cu—Si—Pb—P—Zn alloy.

7. The surface treatment method according to claim 1, wherein the biological reducing substance is reduced glutathione, and the reduced glutathione in the reducing agent solution has a concentration of 0.5 to 2.0 mM.

8. The surface treatment method according to claim 1, wherein the copper or the copper alloy includes an oxide layer, and the oxide layer contains 80.0% or more of $Cu_2O$ and 20.0% or less of CuO in an area from the surface of the oxide layer to 1 μm measured by X-ray photoelectron spectroscopy.

9. A sterilization method comprising: conducting the surface treatment method according to claim 3, and thereafter bringing the article into contact with the surface of an object to sterilize the surface of the object.

10. The sterilization method according to claim 9, wherein the porous body is a woven fabric, a non-woven fabric, or a sponge.

* * * * *